United States Patent [19]

Wakatsuki et al.

[11] Patent Number: 4,736,051

[45] Date of Patent: * Apr. 5, 1988

[54] PROCESS FOR THE PREPARATION OF AN ALKALI METAL SALT OF A DIESTER PHOSPHORIC ACID

[75] Inventors: Junya Wakatsuki; Toru Kato, both of Wakayama; Tomihiro Kurosaki, Osaka; Takashi Imamura, Wakayama, all of Japan

[73] Assignee: Kao Corporation, Tokyo, Japan

[*] Notice: The portion of the term of this patent subsequent to Nov. 18, 2003 has been disclaimed.

[21] Appl. No.: 839,200

[22] Filed: Mar. 13, 1986

[30] Foreign Application Priority Data

| Mar. 20, 1985 | [JP] | Japan | 60-57025 |
| Apr. 4, 1985 | [JP] | Japan | 60-71340 |
| Jul. 31, 1985 | [JP] | Japan | 60-169513 |
| Aug. 28, 1985 | [JP] | Japan | 60-189006 |
| Aug. 29, 1985 | [JP] | Japan | 60-190187 |

[51] Int. Cl.$^4$ .............................................. C07F 9/11
[52] U.S. Cl. .................................................. 558/105
[58] Field of Search ...................................... 558/105

[56] References Cited

U.S. PATENT DOCUMENTS 3,070,620 12/1962 Gold ...................................... 558/105

OTHER PUBLICATIONS

Kosolapoff et al, "Organic Phosphorus Compounds," vol. 6, (1973), p. 232.

*Primary Examiner*—Anton H. Sutto
*Attorney, Agent, or Firm*—Oblon, Fisher, Spivak, McClelland & Maier

[57] ABSTRACT

A process for preparing an alkali metal salt of a phosphoric ester represented by the following general formula (III):

$$R^1O-\underset{\underset{OM}{|}}{\overset{\overset{O}{\|}}{P}}-O-\underset{\underset{R^3}{|}}{\overset{\overset{R^2}{|}}{C}}-\underset{\underset{OH}{|}}{\overset{\overset{R^4}{|}}{C}}-R^5 \quad (III)$$

wherein $R^1$ means an organic group, $R^2$, $R^3$, $R^4$ and $R^5$ denote individually a hydrogen atom or organic group, $R^2$ and $R^4$ may optionally be coupled together into a ring, and M stands for an alkali metal, which comprises reacting a monoalkali metal salt of an organophosphoric monoester, represented by the following general formula (I):

$$R^1O-\underset{\underset{OM}{|}}{\overset{\overset{O}{\|}}{P}}-OH \quad (I)$$

wherein $R^1$ and M have the same meaning as defined above, with an epoxy compound represented by the following general formula (II):

$$\underset{R^3}{\overset{R^2}{\diagdown}}C\underset{O}{\overbrace{\phantom{XXX}}}C\underset{R^5}{\overset{R^4}{\diagup}} \quad (II)$$

wherein $R^2$, $R^3$, $R^4$ and $R^5$ have the same meaning as defined above.

9 Claims, 2 Drawing Sheets

PROCESS FOR THE PREPARATION OF AN ALKALI METAL SALT OF A DIESTER PHOSPHORIC ACID

BACKGROUND OF THE INVENTION

1. Field of the Invention

This invention relates to a preparation process of an alkali metal salt of a phosphoric ester, more specifically to a process for the advantageous preparation of an alkali metal salt of a phosphoric diester by reacting a monoalkali metal salt of a phosphoric monoester and an epoxy compound with good selectivity.

2. Description of the Prior Art

Phosphoric esters are now employed in a wide variety of fields, as detergents, textile conditioners, emulsifiers, rust inhibitors, liquid ion-exchangers, medicaments, etc. Extensive investigations have been being carried out with a view toward introducing one or more structural moieties of different functions in such phosphoric esters while maintaining their inherent functions so that their application field would be expanded further. For example, investigations are now under way to introduce a polymerizable group or a hydrocarbonyl group, each of which contains one or more hetero atoms, e.g., halogen and/or nitrogen atoms so that monomers having phosphoric ester structures and phosphoric esters, each, having a quaternary ammonium salt in the same molecule, such as phospholipids are obtained.

As one of processes for obtaining such compounds, it has been known to subject a phosphoric ester to phosphorochloridate by means of a chlorinating agent such as thionyl chloride or to prepare a phosphoric ester having a phosphorochloridate structure and then to react it with its corresponding organohydroxy compound (see, for example, Japanese Patent Publication No. 30768/1980). The above process is however accompanied by byproduction of hydrochloric gas. Accordingly, it involves difficulties in the treatment of the byproduct, maintenance of the work environment and the like and is hence not suitable as an industrial preparation process.

As another process, may be mentioned to makes use of the reaction between the phosphoric acid group, which each phosphoric ester has, and an epoxy compound. According to this process, the intended compound can be easily obtained from an epoxy compound containing a polymerizable groups or nitrogen atoms and a phosphoric ester. This process is thus the most suitable process for the industrial preparation of such materials. When this process is however applied to a phosphoric monoester, the process produces not only the intended compound, i.e., the corresponding phosphoric diester in which only one hydrocarbyl group having a specific function is selectively introduced in the phosphoric monoester, but also the corresponding phosphoric triester which contains an additional hydrocarbyl group of the same kind introduced therein. It was hence difficult to obtain the intended compound, for example, a polymerizable monomer having surface activity or an analogous monomer in a purified form and with a good yield.

SUMMARY OF THE INVENTION

With the foregoing in view, the present inventors have carried out an extensive investigation. As a result, it has been found that only 1 mole of an epoxy compound can be reacted to 1 mole of a phosphoric monoester by converting the phosphoric monoester into its monoalkali metal salt, leading to completion of the present invention.

The process of this invention is represented by the following reaction formula:

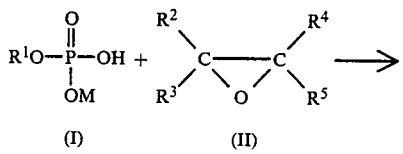

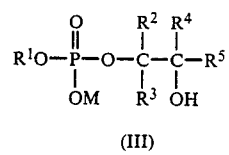

wherein $R^1$ means an organic group, $R^2$, $R^3$, $R^4$ and $R^5$ denote individually a hydrogen atom or organic group, $R^2$ and $R^4$ may optionally be coupled together into a ring, and M stands for an alkali metal.

Namely, this invention provides a process for preparing the alkali metal salt of the phosphoric ester (III) by reacting the monoalkali metal salt of the organophosphoric monoester (I) and the epoxy compound (II).

DETAILED DESCRIPTION OF THE INVENTION AND PREFERRED EMBODIMENTS

Figure 1:
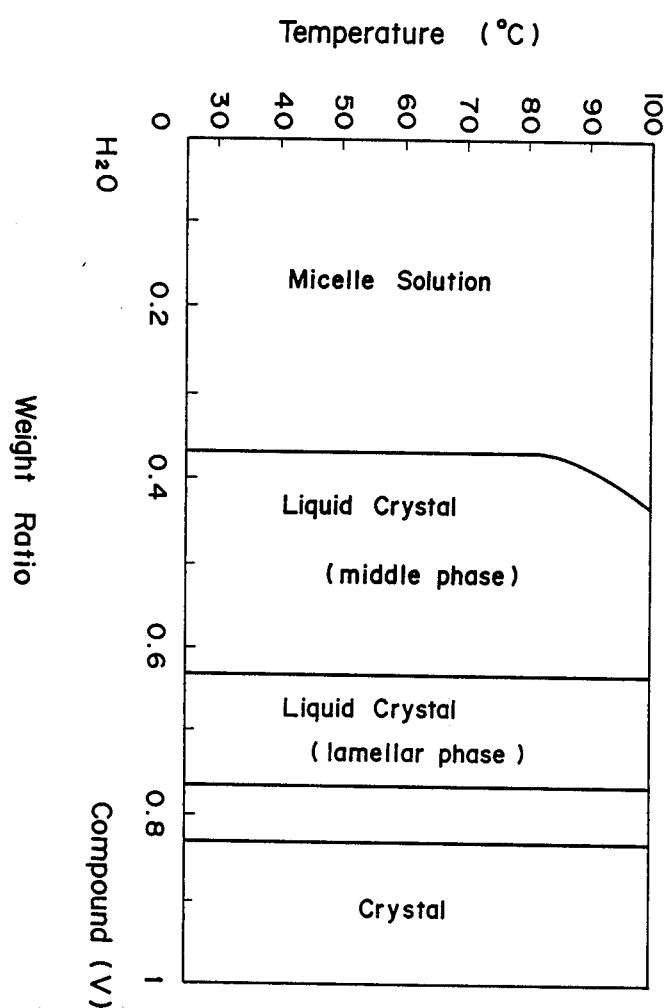
FIG. 1 is a phase diagram of a phosphoric ester compound (V) of this invention/$H_2O$ system.

Illustrative of the monoalkali metal salt of the phosphoric monoester useful in the practice of this invention and represented by the general formula (I) may include monoalkali metal salts of mono(linear or branched)-alkyl or alkenyl phosphates such as monoethyl phosphate, monobutyl phosphate, monooctyl phosphate, monododecyl phosphate, monohexadecyl phosphate, monooctadecyl phosphate, monotetracosyl phosphate, mono-2-ethylhexyl phosphate, mono-2-hexyldecyl phosphate, mono-2-octyldodecyl phosphate, mono-2-tetradecyloctadecyl phosphate, mono-8-methylheptadecyl phosphate, mono(methyl-branched)isostearyl phosphate, monooctenyl phosphate, monodecenyl phosphate, monododecenyl phosphate, monohexadecenyl phosphate, monooctadecenyl phosphate, monotetracosenyl phosphate and monotriacontenyl phosphate; monoalkali metal salts of monoalkylphenyl phosphates such as monooctylphenyl phosphate and monononylphenyl phosphate; monoalkali metal salts of monopolyoxyalkylene alkyl ether phosphate or monopolyoxyalkylene alkenyl ether phosphate such as monopolyoxyethylene(3 moles) dodecyl ether phosphate, monopolyoxypropylene(3 moles) decyl ether phosphate, monopolyoxyethylene(8 moles) polyoxypropylene(3 moles) dodecyl ether phosphate and monopolyoxyethylene(4 moles) octadecenyl ether phosphate; monoalkali metal salts of monopolyoxyalkylene alkylphenyl ether phosphates such as monopolyoxyethylene(5 moles) nonylphenyl ether phosphate and monopolyoxypropylene(2 moles) octylphenyl ether phosphate; monoalkali metal salts of mono-2-hydroxyalkyl phosphates such as mono-2-hydroxydodecyl phosphate and mono-2-hydroxyhexadecyl phosphate; monoalkali metal salts of mono-2-hydroxy-3-alkyloxypropyl phosphates or mono-2-hydroxy-3-alkenyloxypropyl phosphates such as mono-2-hydroxy-3-dodecyloxypropyl phosphate, mono-2-hydroxy-3-mono(methyl-branched)isostearyloxypropyl phosphate and mono-2-hydroxy-3-octadecenyloxypropyl phosphate; monoalkali metal salts of mono(fluorine-containing)alkyl phosphates such as mono(tridecafluorooctyl) phosphate, mono(heptadecafluorodecyl) phosphate, mono(heneicosafluorododecyl) phosphate and mono(pentacosafluorotetradecyl) phosphate; monoalkali metal salts of hexose phosphates and pentose phosphates, in which other hydroxyl groups of the hexose and pentose groups may be blocked by protecting groups, such as glucose-1-phosphate, glucose-6-phosphate, mannose-1-phosphate, galactose-6-phosphate, fructose-1-phosphate and fructose-6-phosphate; etc. It should however be borne in mind that the present invention is not necessarily limited to the use of these monoalkali metal salts. Among these monoalkali metal salts, the sodium and potassium salts are preferred.

As illustrative examples of the epoxy compound useful in the practice of this invention and represented by the general formula (II), may be mentioned glycidyl-containing compounds such as glycidyl (meth)acrylate, allyl glycidyl ether, alkyl glycidyl ethers, glycidyltrialkylammonium halide and the diglycidel ether of bisphenol A; compounds, each, containing an epoxy group at one terminal of the molecule, such as epichlorohydrin, glycidol and the epoxides of α-olefins; compounds, each, containing an epoxy group at a position of the molecule other than both terminals thereof, such as bis(3,4-epoxy-6-methylcyclohexylmethyl) adipate. As particularly-preferred epoxy compound, may be mentioned glycidyl (meth)acrylate and allyl glycidyl ether each of which contains a double bond in its molecule. It should however be borne in mind that the present invention is not necessarily limited to the use of these exemplary epoxy compounds.

No particular limitation is imposed on the preparation process for the monoalkali metal salt of the phosphoric monoester useful in the practice of this invention and represented by the general formula (I). It is however preferred that the monoalkali metal salt of the phosphoric monoester (I) employed in the present invention has a high purity. Namely, inclusion of a salt of a phosphoric diester leads to formation of the intended product with a reduced purity, thereby making it difficult to purify the intended product, in other words, to obtain the intended product in a highly pure form. Furthermore, inclusion of a salt of orthophosphoric acid results in a reduction to the yield of the intended reaction. It also leads to a reduction to the purity of the intended compound and makes difficult the purification of the intended compound to obtain it in a highly pure form. Regarding the purity of the monoalkali metal salt of the phosphoric monoester (I), it is hence preferable to use that having a purity of 90 wt.% or higher.

If the reaction is carried out without converting the phosphoric monoester into its monoalkali metal salt, additional one mole of the epoxy is also caused to react and the corresponding phosphoric triester is byproduced in addition to the intended compound. Thus, the yield of the intended product is reduced. It is therefore not preferable to conduct the reaction without conversion of the phosphoric monoester into its monoalkali metal salt. It is accordingly necessary to use the phosphoric monoester in the form of its monoalkali metal salt upon practice of this invention.

As a solvent to be employed for the reaction, an inert solvent is preferred. Water, methyl alcohol, ethyl alcohol and the like may be mentioned by way of example. Of these, water is preferred. This possibility of use of water as a solvent in extremely preferred from the standpoint of safety when the process of this invention is practiced industrially. Although the epoxy compounds represented by the general formula (II) include many compounds having low solubility to water, use of the phosphoric monoester in the form of its monoalkali metal salt represented by the general formula (I) permits emulsification of the reaction system and hence its uniform reaction with such epoxy compounds of low water-solubility because the phosphoric monoester shows surface activity such as emulsifying property when applied in its salt form.

It is preferable to conduct the reaction at 30°-100° C., notably, 50°-90° C.

In the preparation process of this invention, it is preferable to react the epoxy compound represented by the general formula (II) in an amount of 1-10 moles, especially, 3-5 moles per mole of the monoalkali metal salt of the phosphoric monoester (I).

In the thus-obtained reaction mixture, unreacted epoxy compound (II) or its epoxy-ring hydrolyzed derivative is contained besides the intended alkali metal salt of the phosphoric ester (III). Although the thus-obtained reaction mixture may be used as is depending what end use will be made, it may further be purified into a high-purity form.

Among an alkali metal salt of phosphoric esters available by the process of this invention, preferable esters may be represented by the following formula (IV):

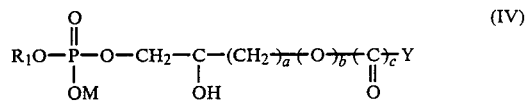

wherein Y means a hydrogen atom, a halogen atom, a hydroxy group, an alkyl or alkenyl group of 1-36 carbon atoms which may partially be substituted by one or more fluorine atoms or an alkylphenyl group having $C_{1-15}$ alkyl group, a stands for a number of 0-2, b and c respectively stand for a number of 0 or 1, $R_1$ and M have the same meaning as defined above.

More preferable esters of the invention are the following compounds (A)-(D).

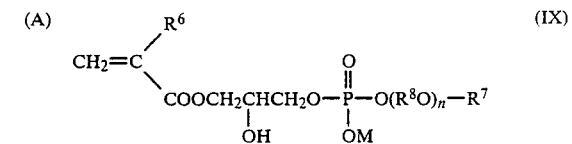

wherein $R^6$ means a hydrogen atom or methyl group, $R^7$ denotes a linear or branched alkyl group of 1-36 carbon atoms, which may optionally be substituted by one or more fluorine atoms, or a phenyl group substituted by linear or branched alkyl groups of 1-15 carbon atoms, $R^8$ is an alkylene group of 2-3 carbon atoms, n stands for a number of 0-30 and M means an alkali metal.

(B)

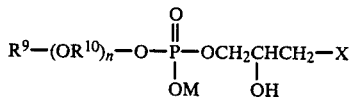

wherein $R^9$ means a linear or branched alkyl or alkenyl group of 1-36 carbon atoms, or a phenyl group substituted by linear or branched alkyl group of 1-15 carbon atoms, $R^{10}$ means an alkylene group of 2 or 3 carbon atoms, X means a halogen atom, and n and M have the same meanings as defined before.

(C)

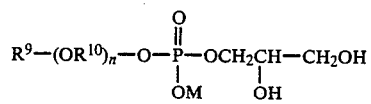

wherein $R^9$, $R^{10}$, n and M have the same meanings as defined before.

(D)

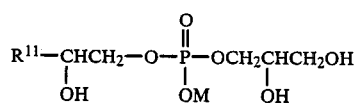

wherein $R^{11}$ means a linear alkyl group of 1-22 carbon atoms, M has the same meanings as defined before.

The compound (A) contains one phosphoric ester structural moiety having surface activity and a polymerizable group per molecule and is hence useful as a material for forming self-organized membranes similar to biological membranes.

The compound (B) is useful as the intermediate for preparation of quarternary ammonium compound of the formula (VIII):

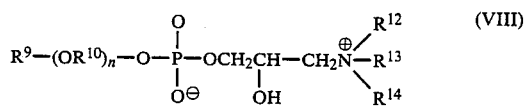

wherein $R^{12}$, $R^{13}$ and $R^{14}$ mean a saturated or unsaturated hydrocarbon group of 1-4 carbon atoms, $R^9$, $R^{10}$, and n have the same meanings defined before. The compound of the formula (VIII) has an excellent surface activity and self-organizability.

The compounds (C) and (D) have an excellent foaming effect and low craft point. Accordingly, these compounds are useful as liquid detergent etc.

When preparing a compound (A) with a polymerizable group per molecule as mentioned above, a polymerization inhibitor or polymerization retarder may also be added upon effecting the reaction. It is preferable to add, for example, hydroquinone monomethyl ether, hydroquinone, 2,2'-methylenebis(4-ethyl-6-t-butylphenol) or the like in an amount of 50-10,000 ppm based on glycidyl methacrylate or glycidyl acrylate.

Purification of such compounds, for example, sodium dodecyl 2-hydroxy-3-methacryloyloxypropylphosphate of the formula (IX) in which $R^7=C_{12}H_{25}$, n=0, $R^6=CH_3$ and M=Na (will hereinafter be called Compound (XIV)) may be carried out in the following manner. After reacting glycidyl methacrylate to an aqueous solution of sodium dodecylphosphate, the reaction product is separated from water by either distilling off water or having the reaction mixture saturated with an electrolyte such as sodium chloride or potassium chloride, extracting organic matter with an organic solvent such as ethyl ether and then distilling off ethyl ether. After extracting unreacted glycidyl methacrylate with a non-polar solvent, for example, n-hexane for its removal, acetone is then added to cause the resultant sodium dodecyl 2-hydroxy-3-methacryloyloxypropylphosphate (XIV) to precipitate so that the sodium salt is separated from the acetone-soluble hydrolyzate of glycidyl methacrylate, i.e., glyceryl methacrylate. In the above-described manner, the intended product can be obtained with good purity.

In addition, the subsequent purification step is facilitated if the unreacted glycidyl methacrylate is completely hydrolyzed subsequent to completion of the reaction.

Further, before using the compound (III), it may be acidified or may then be neutralized with a base such as ammonium, an alkyl amine or an alkanol amine if necessary.

The present invention permits selective introduction of only one hydrocarbyl group having a specific function in a phosphoric monoester without losing the inherent amphiphilic property of the phosphoric monoester and hence enlarges the application field of the phosphoric ester. Moreover, such a phosphoric ester can be industrially produced with extremely great advantages.

It is especially worthy to note that the compounds of the formula (IX) have surface activity and self-organizability because they contain both surface-active and polymerizable groups. This is also appreciated, for example, from the fact that the phase diagrams of the compounds (XIV) in aqueous systems include liquid crystals as shown in FIG. 1.

Further, the polymerizability of the compounds provided by the present invention can be appreciated, for example, from the fact that when a photopolymerization initiator or a usual aqueous polymerization initiator is added to the above-mentioned aqueous solutions of the compounds (XIV) and light or heat is then applied to the resultant aqueous mixtures, the compounds (XIV) are polymerized and the resultant polymers have film-forming properties.

Therefore, the compounds (IX) have surface activities, self-organizability, polymerizability and film-forming properties and show high safety to human bodies. They can thus be used widely in the fields such as engineering and medical science.

The present invention will hereinafter be described by the following Examples.

EXAMPLE 1

(i) Two hundreds grams of monododecyl phosphate having a purity of 97% [0.73 moles, AV1 (mg of KOH necessary for neutralization of 1 g of the phosphoric monoester sample to a first equivalence point) of this sample=210.3, AV2 (mg of KOH necessary for neutralization of 1 g of the phosphoric monoester sample to a second equivalence point)=420.8] was charged into a reactor, to which 750 ml of 1N sodium hydroxide aqueous solution was added, followed by agitation and increasing the temperature to 70° C. to obtain a uniform system. The acid value of the reaction system (mg of KOH necessary for neutralization of 1 g of sample) was found to be 42.9.

(ii) Thereafter, while the reaction system was maintained at 70° C., 533 g (3.75 moles) of glycidyl methacrylate was gradually added, followed by agitation at the temperature for 9 hours. At this time, the acid value of the reaction system was approximately zero, revealing that the reaction was completed. The sample from the reaction system was subjected to the HPLC (high-pressure-liquid chromatography), revealing the peak of unreacted glycidyl methacrylate. Agitation was further continued to a total reaction time of 20 hours, at which glycidyl methacrylate was completely hydrolyzed.

(iii) The reaction solution was then cooled down to room temperature and charged into a separating funnel, followed by saturation with sodium chloride and extraction twice with each 500 g of ethyl ether. The ethyl ether was distilled off under a reduced pressure, and 500 g of acetone was added to the resulting non-volatile liquid residue, followed by allowing to chill at 5° C. After one day, separated crystals were collected and recrystallized from acetone to obtain 178 g of white crystals of sodium dodecyl 2-hydroxy-3-metharyloyloxypropyl phosphate.

$^1$H-NMR:

δ 0.8 ppm (t, 3H, —P—OCH$_2$(CH$_2$)$_{10}$CH$_3$); δ 1.2 ppm (broad s, 20H, —P—OCH$_2$(C$\underline{H}_2$)$_{10}$C$\overline{H}_3$); δ 2.0 ppm (s, 3H, CH$_2$=C—C$\underline{H}_3$); δ 3.7–4.3 ppm (broad, 7H,

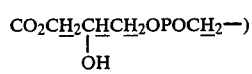

δ 5.5 ppm (broad, s, 1H,

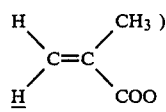

δ 6.1 ppm (broad, s, 1H,

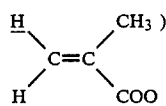

$^{13}$C-NMR:

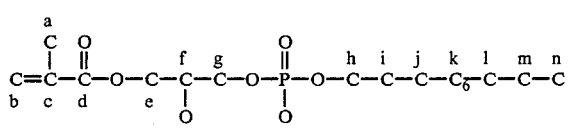

δ (ppm):
n 14.1, a 18.3, m 23.0, j 26.1, ik 30.2, l 32.3, g 65.2, e 68.7, b 126.5, c 136.2

Figure 2:
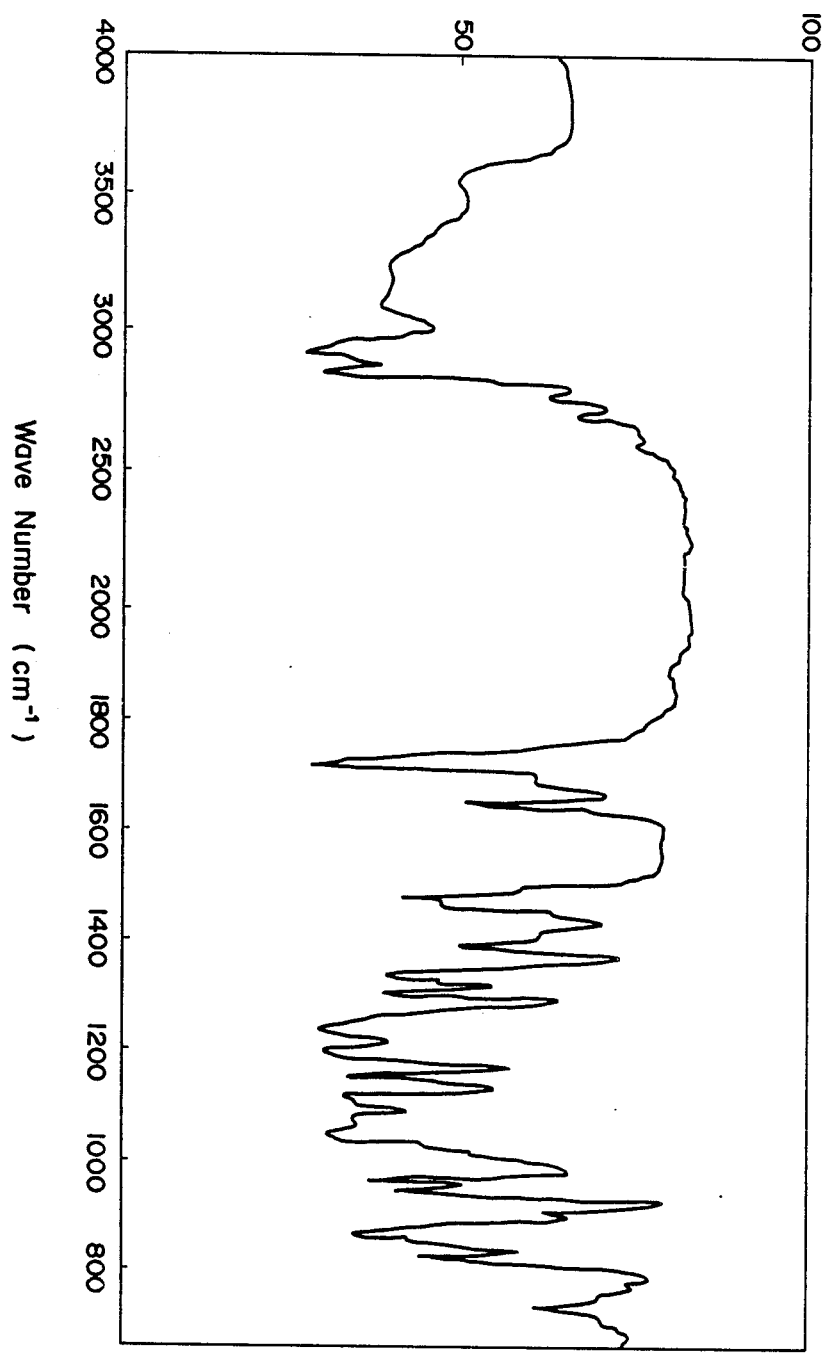
FIG. 2 shows an IR spectrum of the compound (V).

Standard sample: Si(CH$_3$)$_4$
IR (KBr): FIG. 2
Elementary analysis:

|  | C (%) | H (%) | P (%) | Na (%) |
|---|---|---|---|---|
| Found | 52.53 | 8.38 | 7.2 | 5.3 |
| Calculated | 53.02 | 8.43 | 7.2 | 5.3 |

The results of the HPLC analysis revealed that the purity was 98 to 99%.

TEST EXAMPLE 1

To a mixture of the sodium dodecyl 2-hydroxy-3-methacryloyloxypropyl phosphate [Comound (XIV)] obtained in Example 1 and water in 50/50 was added benzoin isobutyl ether, as a photopolymerization initiator, in an amount of 2% of the compound (XIV), followed by light irradiation for 2 hours in a stream of nitrogen, thereby obtaining a colorless transparent rubber-like material. This sample [sample of the mixture of Compound (XIV) and water in 50/50 to which the photopolymerization initiator was added] was sandwiched between slide glasses and thus made thin, followed by light irradiation for 2 hours in the same manner as mentioned above, thereby obtaining a colorless transparent film-like material.

Alternatively, as K$_2$S$_2$O$_8$ polymerization initiator was added to an aqueous solution of about 10% compound (XIV) in an amount of 1% of the compound (XIV), followed by heating at 60° to 70° C. for 4 to 5 hours, thereby obtaining a colorless, transparent, highly viscous aqueous solution. This polymer product was placed on a slide glass and allowed to stand to obtain a colorless transparent film-like material. This polymer product was capable of being gelled in water or methanol.

EXAMPLE 2

(i) In the same manner as in Example 1, 200 g (0.55 moles) of monooctadecyl phosphate having a purity of 97% AV1=160.7, AV2=321.5) was dissolved in 573 ml of 1N sodium hydroxide aqueous solution at 55° C. (at which the acid value of the reaction system was 40.3).

(ii) Thereafter, 407 g (2.86 moles) of glycidyl methacrylate was gradually added, followed by agitation at the temperature for 20 hours. The acid value of the reaction system was approximately zero, revealing that the conversion of the monoalkyl phosphate was approximately 100%.

(iii) Subsequently, the reaction solution was cooled down to 0° C. and the resulting crystals were collected by filtration. The filter cake was washed with acetone and dried to obtain 198 g of white crystals of sodium octadecyl 2-hydroxy-3-methacryloyloxypropyl phosphate.

Elementary analysis:

|  | C (%) | H (%) | P (%) | Na (%) |
|---|---|---|---|---|
| Found | 58.22 | 9.28 | 5.9 | 4.5 |
| Calculated | 58.35 | 9.40 | 6.0 | 4.5 |

The results of the analysis of HPLC revealed that the purity was over 99%.

EXAMPLE 3

(i) Twenty grams (0.057 moles) of mono-2-hexyldecyl phosphate having a purity of 92% (AV1=167.2, AV2=329.8) was dispersed in 59.6 ml of 1N sodium hydroxide aqueous solution (at which the acid value of the reaction system was 39.5).

(ii) Then, 25.4 g (0.178 moles) of glycidyl methacrylate was gradually added at 70° C., followed by agitation at the temperature for 30 hours. The acid value of the reaction system was approximately 1.1, revealing that the conversion of the phosphoric monoester was approximately 97%.

(iii) Subsequently, the reaction solution was analyzed by HPLC with the result that peaks of the hydrolyzate of glycidyl methacrylate and a new product were observed. The product was separated from the reaction solution by HPLC and the solvent was distilled off under reduced pressure to obtain 23.5 g of sodium 2-hexyldecyl 2-hydroxy-3-methacryloyloxypropyl phosphate.

$^1$H-NMR:

δ 0.9 ppm (t, 6H, —CH$_2$C$\underline{H}$$_3$×2); δ 1.3 ppm (broad s, 24H, $$-P-OCH_2CH(C\underline{H}_2)_7CH_3$$
$$(C\underline{H}_2)_5CH_3$$

δ 1.9 ppm (s, 3H, CH$_2$=C—C$\underline{H}$$_3$);
δ 3.4–4.5 ppm (broad, 8H, $$CO_2C\underline{H}_2C\underline{H}C\underline{H}_2OPOC\underline{H}_2C\underline{H}-)$$
$$OH$$

δ 5.5 ppm (broad, s, 1H, $$\underline{H}\diagdown\quad\diagup CH_3$$
$$C=C$$
$$\underline{H}\diagup\quad\diagdown COO$$

)

δ 6.1 ppm (broad, s, 1H, $$\underline{H}\diagdown\quad\diagup CH_3$$
$$C=C$$
$$H\diagup\quad\diagdown COO$$

)

$^{13}$C-NMR:

$$\begin{array}{c}a\\C\quad O\\|\quad\|\\C=C-C-O-C-C-C-O-P-O-C-C-C-C-C-C-C-C-C\\b\quad c\quad d\quad e\ |\quad\ |\quad h\ i\ j\ k\ l\ m\ n\ o\ p\ q\\O\quad O\quad C-C-C-C-C\\j\ k\ n\ o\ p\ q\end{array}$$

δ (ppm):

q 14.2, a 18.3, p 22.7, k 27.0, n 29.8, m 30.1, j 30.8, l 31.1, o 32.0, i 38.6, g 64.8, f 65.6, e 68.2, h 71.1, b 126.3, c 136.1, d 167.5.

Standard sample: Si(CH$_3$)$_4$

|  | C (%) | H (%) | P (%) | Na (%) |
|---|---|---|---|---|
| Found | 56.56 | 8.88 | 6.4 | 5.0 |
| Calculated | 56.78 | 9.12 | 6.4 | 4.7 |

The results of the analysis of HPLC revealed that the purity was 98 to 99%.

EXAMPLE 4

(i) Twenty grams (0.043 moles) of mono-2-decyltetradecyl phosphate having a purity of 94% (AV1=134.2, AV2=267.1) was charged into a reactor, to which 47.8 ml of 1N potassium hydroxide aqueous solution was added and agitated, followed by increasing the temperature to 70° C. to form a uniform dispersion (at which the acid value of the reaction system was 37.9).

(ii) While keeping the reaction system at 70° C., 20.4 g (0.143 moles) of glycidyl methacrylate was gradually dropped, followed by agitation at the temperature for 20 hours. The acid value of the reaction system was approximately 1.5, revealing that the conversion of the phosphoric monoester was about 95%.

(iii) The resulting product was collected by HPLC and the solvent was distilled off under reduced pressure to obtain 23.4 g of potassium 2-decyltetradecyl 2-hydroxy-3-methacryloyloxypropyl phosphate.

Elementary analysis:

|  | C (%) | H (%) | P (%) | Na (%) |
|---|---|---|---|---|
| Found | 60.23 | 9.61 | 5.0 | 6.1 |
| Calculated | 60.55 | 9.84 | 5.0 | 6.4 |

The results of the analysis of HPLC revealed that the purity was 98 to 99%.

EXAMPLE 5

(i) Twenty grams (0.13 moles) of monobutyl phosphate having a purity of 99% (AV1=360.2, AV2=721.3) was charged into a reactor, to which 129 ml of 1 N-sodium hydroxide aqueous solution was added and agitated, followed by dissolution at 70° C. (at which the acid value of the reaction system was 46.7).

(ii) While keeping the reaction system at 70° C., 91.4 g (0.64 moles) of glycidyl methacrylate was gradually dropped, followed by agitation at the temperature for 20 hours. The acid value of the reaction system was approximately zero, revealing that the conversion of the phosphoric monoester was approximately 100%.

(iii) The resulting product was collected by HPLC and the solvent was distilled off under reduced pressure to obtain 37.2 g of sodium butyl 2-hydroxy-3-methacryloyloxypropyl phosphate.

Elementary analysis:

|  | C (%) | H (%) | P (%) | Na (%) |
|---|---|---|---|---|
| Found | 41.03 | 6.28 | 9.6 | 7.2 |
| Calculated | 41.52 | 6.33 | 9.7 | 7.2 |

The results of the analysis of HPLC revealed that the purity was 98 to 99%.

EXAMPLE 6

(i) Twenty grams (0.049 moles) of monotrioxyethylene dodecyl ether phosphate having a purity of 98% (AV1=142.8, AV2=288.2) was charged into a reactor, to which 50.9 ml of 1N potassium hydroxide aqueous solution was added and agitated, followed by dissolution at 70° C. (at which the acid value of the reaction system was 39.5).

(ii) While keeping the reaction system at 70° C., 20.9 g (0.15 moles) of glycidyl methacrylate was gradually dropped, followed by agitation at the temperature for 20 hours. The acid value of the reaction system was approximately 1.5, revealing that the conversion of the phosphoric monoester was approximately 96%.

(iii) The resulting product was collected by HPLC and the solvent was distilled off under reduced pressure to obtain 25.5 g of potassium trioxyethylene dodecyl ether 2-hydroxy-3-methacryloyloxypropyl phosphate.

EXAMPLE 7

(i) Twenty grams (0.035 moles) of monopolyoxyethylene nonylphenyl ether phosphate (average number of moles of ethylene oxide added=5) having a purity of 90% (AV1=97.1, AV2=194.1) was charged into a reactor, to which 34.6 ml of 1N potassium hydroxide aqueous solution was added and agitated, followed by dissolution at 70° C. (at which the acid value of the reaction system was 34.4).

(ii) While keeping the reaction system at 70° C., 24.5 g (0.17 moles) of glycidyl methacrylate was gradually dropped, followed by agitation at the temperature for 20 hours. The acid value of the reaction system was approximately 0, revealing that the conversion of the phosphoric monoester was approximately 100%.

COMPARATIVE EXAMPLE 1

(i) In a reactor, 50 g (0.19 moles) of monododecyl phosphate having a purity of 97% (AV1=209.5, AV2=420.6) was dissolved in 187 ml of tetrahydrofuran, at which the acid value of the reaction system was AV1=48.8, AV2=97.9.

(ii) While keeping the reaction system at 70° C., 134 g (0.94 moles) of glycidyl methacrylate was gradually dropped, followed by agitation at the temperature for 1 hour. The acid value of the reaction system was AV1=7.6, AV2=10.3, revealing that the reaction system contained 9 mole % of unreacted phosphoric monoester and 16 mole % of the corresponding phosphoric diester and 75 mole % of the corresponding phosphoric triester were formed. The agitation was continued further to a total reaction time of 4 hours, at which the acid value was measured. It was found to be approximately 0, revealing that the phosphoric monoester reacted approximately to 100% and was converted in its entirety into the phosphoric triester.

COMPARATIVE EXAMPLE 2

(i) In a reactor, 50 g (0.19 moles) of monododecyl phosphate having a purity of 97% (AV1=209.5, AV2=420.6) was dissolved in 187 ml of tetrahydrofuran, at which the acid value of the reaction system was AV1=48.8, AV2=97.9.

(ii) While keeping the reaction system at 70° C., 27 g (0.19 moles) of glycidyl methacrylate was gradually dropped, followed by agitation at the temperature for 5 hours. The acid value of the reaction system was AV1=30.8, AV2=49.0, revealing that the reaction system contained 42 mole % of unreacted phosphoric monoester and 29 mole % of the corresponding phosphoric diester and 29 mole % of the corresponding phosphoric triester were formed.

EXAMPLE 8

(i) Charged in a reactor was 20.0 g of monododecyl phosphate having a purity of 97% [0.073 moles, AV1 of this sample=210.3, AV2=420.8], to which 75.0 ml of 1N sodium hydroxide aqueous solution was added, followed by agitation and increasing the temperature to 70° C. to obtain a uniform system. The acid value of the reaction system was found to be 42.9.

(ii) Thereafter, while the reaction system was maintained at 70°-80° C., 24.3 g of glycidol [its oxirane value (mg, expressed in terms of mg of potassium hydroxide, of the amount of hydrochloric acid consumed upon chlorohydrination of oxirane rings in its 1-gram sample)=683.7] was gradually added, followed by agitation at the temperature for 6 hours. At this time, the acid value of the reaction system was approximately zero, revealing that the reaction was completed.

(iii) The reaction solution was then poured into 500 g of acetone, followed by its refrigeration at 5° C. to crystallize the reaction product. One day later, separated crystals were collected by filtration and then washed with acetone to obtain 18.3 g of sodium dodecyl glyceryl phosphate as white crystals (yield: 69.2%).

$^1$H-NMR (D$_2$O, internal standard: sodium trimethylsilylpropylsulfonate):

δ0.8 ppm (t, 3H, —P—OCH$_2$(CH$_2$)$_{10}$CH$_3$); δ1.3 ppm (broad s, 20H, —P—OCH$_2$(CH$_2$)$_{10}$CH$_3$); δ3.4–3.9 ppm (m, 7H, HO—CH$_2$CHCH$_2$OPOCH$_2$—)
$\qquad\qquad\quad$ |
$\qquad\qquad\quad$ OH $^{13}$C-NMR (D$_2$O, internal standard: dioxane):

$$\underset{\text{OH}}{\overset{i\ \ k\ \ j}{HO-C-C-C}}-O-\overset{\overset{O}{\|}}{\underset{O}{P}}-O-\overset{j}{C}-\overset{g}{C}-\overset{c}{C}-\overset{d}{C}(\overset{f}{C})_{\overline{7}}\overset{e}{C}-\overset{h}{C}-\overset{b}{C}-\overset{a}{C}$$

δ(ppm):
a 14.6, b 23.4, c 26.5, d 29.3, e 30.3, f 30.4, g 31.5, h 32.7, i 63.1, j 66.8–67.1, k 71.7.

Elementary analysis:

|  | C (%) | H (%) | P (%) | Na (%) |
|---|---|---|---|---|
| Found | 49.3 | 8.5 | 8.5 | 6.7 |
| Calculated | 49.7 | 8.9 | 8.6 | 6.4 |

COMPARATIVE EXAMPLE 3

(i) Charged in a reactor was 100.0 g (0.36 moles) of monododecyl phosphate having a purity of 97% (AV1=210.3, AV2=420.8), followed by its dissolution in 337 g of tetrahydrofuran.

(ii) While keeping the reaction system at 60° C., 150 g of glycidol (oxirane value=683.7) was gradually added, followed by their reaction at 70° C. for 2 hours. The acid value of the reaction system was AV1=4.4, AV2=6.0, revealing that the reaction system contained about 4.5 mole % of unreacted monododecyl phosphate and about 8.1 mole % of the corresponding phosphoric diester, i.e., dodecyl glyceryl phosphate and about 87.4 mole % of the corresponding phosphoric triester, i.e., dodecyl diglyceryl phosphate were formed.

COMPARATIVE EXAMPLE 4

(i) Charged in a reactor was 50.0 g (0.182 moles) of monododecyl phosphate having a purity of 97% (AV1=210.3, AV2=420.8), followed by its dissolution in 67.7 g of tetrahydrofuran.

(ii) While keeping the reaction system at 60° C., 36.9 g of glycidol (oxirane value=683.7) was gradually dadded, followed by their reaction at 70° C. for 10 hours. The acid value of the reaction system was AV1=39.6, AV2=57.3, revealing that the reaction system contained about 27 mole % of unreacted monododecyl phosphate and about 33 mole % of the corresponding phosphoric diester, i.e., dodecyl glyceryl phosphate and about 40 mole % of the corresponding phosphoric triester, i.e., dodecyl diglyceryl phosphate were formed.

EXAMPLE 9

(i) Twenty grams (0.057 moles) of mono-2-hexyldecyl phosphate having a purity of 92% (AV1=167.2, AV2=329.8) was dispersed in 59.6 ml of 1N sodium hydroxide aqueous solution at 55° C. (at which the acid value of the reaction system was 39.5).

(ii) At 80° C., 16.5 g (0.178 moles) of epichlorohydrin was gradually added to the suspension, followed by agitation at the temperature for 8 hours. The acid value o the reaction system was approximately zero, revealing that the conversion of the phosphoric monoester was approximately 100%.

(iii) The reaction solution was analyzed by HPLC. The chromatogram showed peaks corresponding respectively to the hydrolyzate of epichlorohydrin and a new reaction product. The reaction product was isolated from the reaction solution by HPLC and the solvent was distilled off under reduced pressure, thereby obtaining 20.5 g of sodium 2-hexyldecyl 2-chloropropyl phosphate (yield: 82.3%).

Elementary analysis:

|  | C (%) | H (%) | P (%) | Na (%) | Cl (%) |
|---|---|---|---|---|---|
| Found | 52.05 | 8.79 | 7.1 | 5.8 | 8.37 |
| Calculated | 52.23 | 9.00 | 7.1 | 5.3 | 8.11 |

EXAMPLE 10

(i) Twenty grams (0.13 moles) of monobutyl phosphate having a purity of 99% (AV1=360.6, AV2=721.3) was charged in a reactor, to which 129 ml of 1N sodium hydroxide aqueous solution was added, followed by agitation and heating of the resultant mixture at 70° C. to dissolve the phosphate (at which the acid value of the reaction system was 46.7).

(ii) While keeping the reaction system at 70° C., 59.2 g (0.64 moles) of epichlorohydrin was gradually dropped, followed by agitation at the temperature for 20 hours. The acid value of the reaction system was approximately zero, revealing that the conversion of the phosphoric monoester was approximately 100%.

(iii) The reaction product was collected by HPLC, from which the solvent was distilled off under reduced pressured to obtain 30.2 g of sodium butyl 2-hydroxy-3-chloropropyl phosphate (yield: 86.5%).

Elementary analysis:

|  | C (%) | H (%) | P (%) | Na (%) | Cl (%) |
|---|---|---|---|---|---|
| Found | 31.14 | 5.38 | 11.2 | 8.9 | 13.55 |
| Calculated | 31.30 | 5.63 | 11.5 | 8.6 | 13.20 |

As a result of an HPLC analysis, the purity was found to be 98–99%.

EXAMPLE 11

(i) Twenty grams (0.049 moles) of monotrioxyethylene dodecyl ether phosphate having a purity of 98% (AV1=142.8, AV2=288.2) was charged in a reactor, to which 50.9 ml of 1N potassium hydroxide aqueous solution was added, followed by agitation and heating of the resultant mixture at 80° C. to dissolve the phosphate (at which the acid value of the reaction system was 39.5).

(ii) While keeping the reaction system at 80° C., 22.7 g (0.25 moles) of epichlorohydrin was gradually dropped, followed by agitation at the temperature for 6 hours. The acid value of the reaction system was approximately zero, revealing that the conversion of the phosphoric monoester was approximately 100%.

(iii) The reaction product was collected by HPLC, from which the solvent was distilled off under reduced pressure to obtain 19.3 g of potassium trioxyethylene dodecyl ether 2-hydroxy-3-chloropropyl phosphate (yield: 74.5%).

Elementary analysis:

|  | C (%) | H (%) | P (%) | K (%) | Cl (%) |
|---|---|---|---|---|---|
| Found | 47.39 | 7.95 | 5.9 | 7.3 | 6.99 |
| Calculated | 47.68 | 8.14 | 5.9 | 7.4 | 6.72 |

As a result of an HPLC analysis, the purity was found to be 98–99%.

EXAMPLE 12

(i) Twenty grams (0.060 moles) of mononylphenyl phosphate having a purity of 90% (AV1=168.2, AV2=338.2) was charged in a reactor, to which 60.0 ml of 1N potassium hydroxide aqueous solution was added, followed by its uniform dispersion at 80° C. (at which the acid value of the reaction system was 42.3).

(ii) While keeping the reaction system at 80° C., 27.8 g (0.30 moles) of epichlorohydrin was gradually dropped, followed by agitation at the temperature for 6 hours. The acid value of the reaction system was approximately zero, revealing that the conversion of the phosphoric monoester was approximately 100%.

(iii) The reaction product was collected by HPLC, from which the solvent was distilled off under reduced pressured to obtain 18.1 g of potassium nonylphenyl 2-hydroxy-3-chloropropyl phosphate (yield: 70.0%).

Elementary analysis:

|  | C (%) | H (%) | P (%) | K (%) | Cl (%) |
|---|---|---|---|---|---|
| Found | 49.83 | 6.56 | 7.3 | 9.0 | 8.59 |
| Calculated | 50.17 | 6.78 | 7.2 | 9.1 | 8.23 |

As a result of an HPLC analysis, the purity was found to be 98–99%.

EXAMPLE 13

(i) Twenty grams (0.052 moles) of monooctadecenyl phosphate having a purity of 90% (AV1=165.0, AV2=323.2) was charged in a reactor, to which 58.8 ml of 1N potassium hydroxide aqueous solution was added, followed by its agitation and uniform dispersion at 80° C. (at which the acid value of the reaction system was 40.2).

(ii) While keeping the reaction system at 80° C., 24.1 g (0.26 moles) of epichlorohydrin was gradually dropped, followed by agitation at the temperature for 6 hours. The acid value of the reaction system was approximately zero, revealing that the conversion of the phosphoric monoester was approximately 100%.

(iii) The reaction product was collected by HPLC, from which the solvent was distilled off under reduced pressured to obtain 16.9 g of potassium octadecenyl 2-hydroxy-3-chloropropyl phosphate (yield: 67.8%).

Elementary analysis:

|  | C (%) | H (%) | P (%) | K (%) | Cl (%) |
|---|---|---|---|---|---|
| Found | 52.08 | 8.52 | 6.5 | 8.1 | 7.63 |
| Calculated | 52.65 | 8.63 | 6.5 | 8.2 | 7.40 |

As a result of an HPLC analysis, the purity was found to be 98–99%.

EXAMPLE 14

(i) Charged in a reactor were 500 parts by weight of monododecyl phosphate, followed by an addition of 1950 parts by weight of 1N potassium hydroxide aqueous solution. The resultant mixture was agitated and heated to 60° C. to homogenize the mixture.

(ii) While keeping the reaction system near 60° C., a solution of 1390 parts by weight of glycidyltrimethylammonium chloride dissolved in 750 parts by weight of water was gradually dropped, followed by their reaction at 60° C. for 5 hours.

(iii) After completion of the reaction, the reaction mixture was filtered to remove floating impurities. The filtrate was caused to pass through an electrodialyzer to remove ionic impurities, followed by removal of water from the electrodialyzed solution by distillation to obtain a very hygroscopic compound as white powder. Its analysis results were as given below, thereby confirming it as the intended compound. Its purity was over 99%.

Elementary analysis:

|  | C (%) | H (%) | N (%) | P (%) |
|---|---|---|---|---|
| Found | 56.6 | 10.4 | 3.6 | 7.4 |
| Calculated | 56.7 | 10.6 | 3.7 | 8.1 |

$^1$H-NMR (Solvent: D$_2$O):
δ0.6–2.0 ppm (m, 25H); δ3.27 ppm (s, 9H); δ3.44–4.20 ppm (m, 5H); δ4.43 ppm (broad s, 1H).

$^{13}$C-NMR (solvent: D$_2$O):

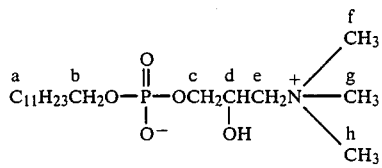

δ (ppm):
a: 14.13, 22.98, 30.29, 31.19, 32.41, b: 66.35, c: 65.70, d: 65.22, e: 67.49, f, g, h: 54.50.

Miscellaneous Analysis:
Acid value (KOH mg/g): 0.73 (automatic titration)
Hydroxyl value (KOH mg/g): 151 (ditto)
Oxirane value (KOH mg/g): −5.7 (ditto)
Chlorine anions (wt.%): 0.01 (Volhard method)
Whole chlorine (wt.%): 0.01 (ditto)
Water content (wt.%): 1.77

EXAMPLE 15

α-D-Glucopyranose
1-(2-hydroxy-3-N,N,N-trimethylammoniopropyl phosphate)

Charged in a reactor were 100 parts by weight of monosodium α-D-glucose-1-phosphate and 89.8 parts by weight of water, followed by heating of the contents to 60° C. While maintaining the reaction system at 60° C., a solution of 161 parts by weight of glycidyltrimethylammonium chloride dissolved in 143 parts by weight of water was gradually dropped, followed by their reaction at 60° C. for 4 hours. After completion of the reaction, the reaction mixture was filtered to remove floating impurities. The filtrate was caused to pass through an electrodialyzer to remove ionic impurities, followed by removal of water from the electrodialyzed solution by distillation to obtain 108 parts by weight of white powdery compound. Its analysis results were as given below, thereby confirming it as the intended compound.

Elementary analysis (molecular formula: C$_{12}$H$_{26}$O$_{10}$NP):

|  | C (%) | N (%) | H (%) | P (%) |
|---|---|---|---|---|
| Found | 38.2 | 3.7 | 6.6 | 8.0 |
| Calculated | 38.4 | 3.7 | 6.9 | 8.3 |

$^1$H-NMR (solvent: D$_2$O):
δ3.22 ppm (s, 9H); δ3.29–4.10 ppm (m, 12H); δ5.40 ppm (q, 1H).

Miscellaneous Analysis:
Chlorine anions (wt.%): 0.08
Whole chlorine (wt.%): 0.09
Water content (wt.%): 1.32

EXAMPLE 16

α-D-Mannopyranose
1-(2-hydroxy-3-N,N,N-trimethylammoniopropyl phosphate)

Charged in a reactor were 100 parts by weight of disodium α-D-mannose-1-phosphate, followed by its dissolution in a mixture of 82.2 parts by weight of 4N hydrochloric acid and 85.8 parts by weight of water. The resultant solution was heated to 60° C. While maintaining the reaction system at 60° C., a solution of 148 parts by weight of glycidyltrimethylammonium chloride dissolved in 217 parts by weight of water was gradually dropped, followed by their reaction at 60° C. for 5 hours. After completion of the reaction, the reaction mixture was purified in the same manner as in Example 9 to obtain 98 parts by weight of the intended compound.

Elementary analysis (molecular formula: C$_{12}$H$_{26}$O$_{10}$NP):

|  | C (%) | N (%) | H (%) | P (%) |
|---|---|---|---|---|
| Found | 37.9 | 3.5 | 6.6 | 8.0 |
| Calculated | 38.4 | 3.7 | 6.9 | 8.3 |

$^1$H-NMR (solvent: D$_2$O): δ3.18 ppm (s, 9H); δ3.25–4.15 ppm (m, 12H); δ5.38 ppm (q, 1H).

Miscellaneous Analysis:
Chlorine anions (wt.%): 0.11
Whole chlorine (wt.%): 0.13

Water content (wt.%): 1.43

EXAMPLE 17

Potassium α-D-glucopyranose 1-(2,3-dihydroxypropyl phosphate)

In a reactor, 89 g (0.3 moles) of monopotassium α-D-glucose-1-phosphate was dissolved in 64 g of water and the resultant solution was heated to 60° C. Thereafter, while maintaining the reaction system at 60° C., 67 g (0.9 moles) of glycidol was gradually dropped, followed by their reaction at 60° C. for 9 hours. after completion of the reaction, the reaction mixture was filtered to remove floating impurities. The filtrate was then caused to pass through an ultrafiltration apparatus (equipped with a polysulfone-type ultrafilter membrane; KCl inhibition rate: 45%) to remove impurities, followed by lyophilization to obtain 45 g (0.12 moles) of the intended compound. Conversion: 100%. Yield of the isolated potassium salt: 40%.

EXAMPLE 18

95.5 g (0.19 moles) of heptadecafluorodecyl phosphate having a purity of 97% (AV1=108.9, AV2=217.0) was charged into a reactor, to which 185 ml of 1N sodium hydroxide aqueous solution was added. The resulting mixture was then agitated and heated to 70° C. to make a uniform system. The acid value of the reaction system was 36.8. While keeping the reaction system at 70° C., 104.5 g (0.74 moles) of glycidyl methacrylate was gradually added, followed by agitation at the temperature for 9 hours, at which the acid value of the reaction system was approximately zero, revealing that the reaction was completed. The sample was analyzed by HPLC with the result that a peak of unreacted glycidyl methacrylate was observed. Agitation was further continued to a total time of 20 hours, at which it was found that glycidyl methacrylate was hydrolyzed completely and that peaks of glyceryl methacrylate which was a hydrolyzed product at the epoxy moiety and of an intended compound were recognized. The reaction solution was cooled down to room temperature, to which 200 g of acetone was added, followed by cooling to −5° C. to obtain 92 g of heptadecafluorodecyl 2-hydroxy-3-methacryloyloxy-propyl phosphate (yield: 70%).

$^1$H-NMR.

δ2.0 ppm (s, 3H, CH$_2$=C—C$\underline{H}_3$); δ2.6 ppm (tt, 2H, —P—OCH$_2$C$\underline{H}_2$CF$_2$—); δ3.5–4.5 ppm (m, 6H, CO$_2$C$\underline{H}_2$C$\underline{H}$C$\underline{H}_2$OPOC$\underline{H}_2$—)
         |
         OH δ5.6 ppm (broad, s, 1H,

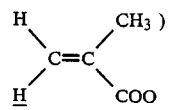
)

δ6.1 ppm (broad, s, 1H,

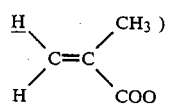
)

$^{13}$C-NMR:

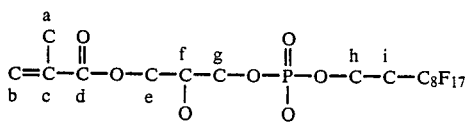

δ (ppm):
a 18.5, i 33.4, h 58.7, e 66.5, g 67.6, f 69.9, b 126.5, c 137.6, d 168.9

Standard sample: Si(CH$_3$)$_4$

Elementary analysis:

|  | C (%) | H (%) | F (%) | P (%) | Na (%) |
|---|---|---|---|---|---|
| Found | 28.53 | 2.33 | 45 | 4.3 | 3.3 |
| Calculated | 28.83 | 2.13 | 46 | 4.4 | 3.3 |

As a result of an HPLC analysis, the purity was found to be 98–99%.

TEST EXAMPLE 2

K$_2$S$_2$O$_8$ as a polymerization initiator was added to an aqueous solution of about 10% of sodium heptadecafluorodecyl 2-hydroxy-3-methacryloyloxypropyl phosphate [Compound (VI)] obtained in Example 18 in an amount of 1% of the compound (VI), followed by heating at 60° to 70° C. for 4 to 5 hours, thereby obtaining a colorless, transparent, highly viscous aqueous solution. The polymerized product was placed on a slide glass and allowed to stand to obtain a colorless transparent film-like material.

The highly viscous aqueous solution had a anisotropic property and a systematic liquid crystal structure.

EXAMPLE 19

(i) Twenty grams (0.025 moles) of 2-tridecafluorohexyltridecafluorodecyl phosphate having a purity of 92% (AV1=70.1, AV2=139.8) was dispersed in 24.8 ml of 1N sodium hydroxide aqueous solution (at which the acid value of the reaction system was 31.1), to which 14.2 g (0.10 moles) of glycidyl methacrylate was gradually added at 70° C., followed by agitation at the temperature for 30 hours. At this time, the acid value of the reaction system was approximately zero, revealing that the conversion of the phosphoric monoester was approximately 100%. The reaction solution was analyzed by HPLC, revealing that peaks of the hydrolyzate of glycidyl methacrylate and a new compound were found. The resulting product was collected by HPLC and the solvent was distilled off under reduced pressure to obtain 21.5 g of sodium 2-tridecafluorohexyltridecafluorodecyl-2-hydroxy-3-methacryloyloxypropyl phosphate (yield: 89%).

Elementary analysis:

|  | C (%) | H (%) | F (%) | P (%) | Na (%) |
|---|---|---|---|---|---|
| Found | 28.71 | 1.52 | 50 | 3.1 | 2.7 |
| Calculated | 29.07 | 1.49 | 52 | 3.3 | 2.4 |

As a result of an HPLC analysis, the purity was found to be 98–99%.

EXAMPLE 20

20.0 g (0.073 moles) of monododecyl phosphate having a purity of 97% (AV1=210.3, AV2=420.8) was charged into a reactor, to which 75.0 ml of 1N sodium hydroxide aqueous solution was added and agitated, followed by heating to 70° C. to make a uniform system. The acid value of the reaction system was 42.9. While keeping the reaction system at 70° to 80° C., 24.0 g of glycidol [the oxirane value (the amount of HCl to be consumed for chrolhydrination of oxirane ring present in 1 g of sample, represented by mg of KOH) of this sample was 683.7] was gradually added, followed by agitation at the temperature for 6 hours, at which the acid value of the reaction system was approximately zero, revealing that the reaction was completed. The reaction solution was poured into 1000 g of acetone, followed by cooling to 5° C. and maintaining at the temperature to obtain crystals. After 1 day, separated crystals were collected by filtration and washed by acetone to obtain 18.3 g (yield 69.2%) of white crystals of sodium dodecylglyceryl phosphate.

$^1$H NMR (D$_2$O, internal standard: 3-trimethylsilyl-propan sulphonic acid soda); δ 0.8 ppm (t, 3H, —P—OCH$_2$(CH$_2$)$_{10}$C$\underline{H}_3$); δ 1.3 ppm (broad s, 20H, —P—OCH$_2$(C$\underline{H}_2$)$_{10}$C$\overline{H}_3$); δ 3.4–3.9 ppm

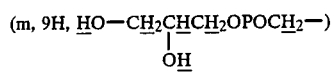

(m, 9H, H$\underline{O}$—C$\underline{H}_2$C$\underline{H}$CH$_2$OPOC$\underline{H}_2$—)
      |
      O$\underline{H}$ $^{13}$C NMR (D$_2$O, internal standard: dioxane)

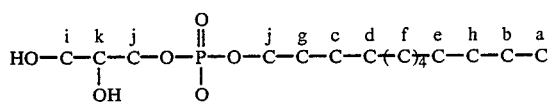

δ ppm
a; 14.6, b; 23.4, c; 26.5, d; 29.3, e; 30.3, f; 30.4, g; 31.5, h; 32.7, i; 63.1, j; 66.8–67.1, k; 71.7

Elementary Analysis:

|  | C (%) | H (%) | P (%) | Na (%) |
|---|---|---|---|---|
| Found | 49.3 | 8.5 | 8.5 | 6.7 |
| Calculated | 49.7 | 8.9 | 8.6 | 6.4 |

The lather amount and craft point of sodium dodecylglyceryl phosphate were measured. The results are shown in Table 1. The results reveal that the lather amount of sodium dodecylglyceryl phosphate is almost the same as those of sodium dodecyl phosphates, comparative ones, on the other hand, craft point of sodium dodecylglyceryl phosphate is extremely lower than those of sodium dodecyl phosphates.

The lather amount was measured according to the following manner. An aqueous solution containing 5% of surface active agent is prepared and 100 g of the aqueous solution is poured into a measuring cylinder, followed by agitation for 30 seconds by agitator. After agitation, the aqueous solution is placed as it is for 10 seconds, followed by subjecting to measurement of the lather volume. The revolution of the agitator is 1000 rpm and the agitator paddles are reversely rotated every 5 seconds. Temperature was maintained 40° C. during the measurement.

TABLE 1

|  | lather amount (lather Vol. ml) | craft point (°C.) |
|---|---|---|
| Sodium 1 dodecyl phosphate | 260 | 32 |
| Sodium 2 dodecyl phosphate | 230 | 20 |
| Sodium dodecylglyceryl phosphate | 240 | <0 |

EXAMPLE 21

10.0 g (0.030 moles) of monohexadecyl phosphate having a purity of 96% (AV1=173.6, AV2=344.0) was charged into a reactor, to which 30.9 ml of 1N sodium hydroxide aqueous solution was added and agitated, followed by heating to 70° C. to make a uniform system. The acid value of the reaction system was 40.3. While keeping the reaction system at 70° to 80° C., 9.8 g of glycidol (the oxirane value=683.7) was gradually added, followed by agitation at the temperature for 6 hours, at which the acid value of the reaction system was approximately zero, revealing that the reaction was completed. The reaction solution was poured into 300 g of acetone, followed by cooling to 5° C. and maitaining the temperature to obtain crystals. After one day, separated crystals were collected by filtration and washed by acetone to obtain 8.2 g (yield 65.3%) of white crystals of sodium hexadecylglyceryl phosphate.

Elementary Analysis:

|  | C (%) | H (%) | P (%) | Na (%) |
|---|---|---|---|---|
| Found | 53.85 | 9.27 | 7.2 | 5.3 |
| Calculated | 54.48 | 9.56 | 7.4 | 5.5 |

EXAMPLE 22

20 g (0.057 moles) of mono-2-hexyldecyl phosphate having a purity of 92% (AV1=167.2, AV2=329.8) was charged into a reactor, to which 59.6 ml of 1N sodium hydroxide aqueous solution was added. At this moment, the acid value of the reaction system was 39.5. While keeping the reaction system at 70° C., 14.0 g of glycidol (the oxirane value=683.7) was gradually added, followed by agitation at the temperature for 8 hours, at which the acid value of the reaction system was 0.7, revealing that the conversion of the phosphric monoester was approximately 98%. The reaction solution was analyzed by HPLC. The chromatography showed peaks corresponding to a new reaction product. The reaction product was isolated from the reaction solution by HPLC and the solvent was distilled off under reduced pressure, thereby obtaining 19.6 g of sodium 2-hexyldecylglyceryl phosphate (yield: 82.1%).

Elementary Analysis:

|  | C (%) | H (%) | P (%) | Na (%) |
|---|---|---|---|---|
| Found | 54.32 | 9.44 | 7.5 | 5.5 |
| Calculated | 54.48 | 9.56 | 7.4 | 5.5 |

EXAMPLE 23

20 g (0.13 moles) of monobutyl phosphate having a purity of 99% (AV1=360.6, AV2=721.3) was charged into a reactor, to which 129 ml of 1N sodium hydroxide aqueous solution was added and agitated, followed by heating to 70° C. to make a uniform system. At this moment, the acid value of the reaction system was 46.7. While keeping the reaction system at 70° C., 42.7 g of glycidol (the oxirane value=683.7) was gradually dropped, followed by agitation at the temperature for 6 hours, at which the acid value of the reaction system was approximately zero, revealing that the conversion of phosphoric monoester was almost 100%. The reaction product was isolated from the reaction solution by HPLC and the solvent was distilled off under reduced pressure, thereby obtaining 26.5 g of sodium butylglyceryl phosphate (yield: 81.5%).

Elementary Analysis

|  | C (%) | H (%) | P (%) | Na (%) |
| --- | --- | --- | --- | --- |
| Found | 32.98 | 6.39 | 12.5 | 9.1 |
| Calculated | 33.61 | 6.45 | 12.4 | 9.2 |

EXAMPLE 24

To 71.4 ml of 1N sodium hydroxide aqueous solution, 20 g (0.067 moles) of mono-2-hydroxydodecyl phosphate having a purity of 95% (AV1=200.2, AV2=400.5) was added and dissolved, at which the acid value of the reaction system was 42.4. While keeping the reaction system at 70° C., 22.0 g of glycidol (the oxirane value=42.4) was gradually charged, followed by agitation at the temperature for 8 hours. The acid value of the reaction system was approximately zero, revealing that the reaction rate of the phosphoric monoester was almost 100%. The reaction solution was analyzed by HPLC. The choromatography showed peaks corresponding to a new reaction product. The reaction product was isolated from the reaction solution by HPLC and the solvent was distilled off under reduced pressure, thereby obtaining 20.8 g of sodium 2-hydroxydodecylglyceryl phosphate (yield: 81.7).

Elementary Analysis:

|  | C (%) | H (%) | P (%) | Na (%) |
| --- | --- | --- | --- | --- |
| Found | 47.46 | 8.32 | 8.2 | 6.3 |
| Calculated | 47.61 | 8.52 | 8.2 | 6.1 |

EXAMPLE 25

20 g (0.049 moles) of mono trioxyethylenedodecylether phosphate having a purity of 98% (AV1=142.8, AV2=288.2) was charged into a reactor, to which 50.9 ml of 1N potassium hydroxide aqueous solution was added and agitated, followed by dissolution at 70° C., at which the acid value of the reaction system was 39.5). While keeping the reaction system at 70° C., 16.1 g of glycidol (the oxirane value=683.7) was gradually dropped, followed by agitation at the temperature for 6 hours. The acid value of the reaction system was approximately zero, revealing that the reaction rate of the phosphoric monoester was almost 100%. The resulting product was collected by HPLC and the solvent was distilled off under reduced pressure to obtain 20.8 g of potassium trioxyethylendodecylglyceryl phosphate (yield: 83.4%).

Elementary Analysis:

|  | C (%) | H (%) | P (%) | K (%) |
| --- | --- | --- | --- | --- |
| Found | 48.99 | 8.60 | 6.2 | 7.8 |
| Calculated | 49.39 | 8.68 | 6.1 | 7.7 |

EXAMPLE 26

20 g (0.035 moles) of monopolyoxyethylene nonylphenylether phosphate (average moles of added ethyleneoxide=5) having a purity of 90% (AV1=97.1, AV2=194.1) was charged into a reactor, to which 34.6 ml of 1N potassium hydroxide aqueous solution was added and agitated, followed by dissolution at 70° C., at which the acid value of the reaction system was 34.4. While keeping the reaction system at 70° C., 11.5 g of glycidol (the oxirane value=683.7) was gradually dropped, followed by agitation at the temperature for 6 hours. The acid value of the reaction system was approximately zero, revealing that 100% of the phosphoric monoester had converted.

REFERENCE 1

100.0 g (0.36 moles) of monododecyl phosphate having a purity of 97% (AV1=210.3, AV2=420.8) was charged into a reactor, to which 337 g of tetrahydrofurane was added, followed by dissolution. While keeping the reaction system at 60° C., 150 g of glycidol (the oxirane value=683.7) was gradually added, followed by proceeding reaction at 70° C. for 2 hours. AV1 and AV2 of the reaction system were 4.4 and 6.0 respectively, revealing that approximately 4.5 mol% of unreacted monododecyl phosphate, approximately 8.1 mol% of dodecylglyceryl phosphate which is a diester phosphate and approximately 87.4 mole% of dodecyldiglyceryl phosphate which is a triester phosphate were produced.

REFERENCE 2

50.0 g (0.182 moles) of monododecyl phosphate having a purity of 97% (AV1=210.3, AV2=420.8) was charged into a reactor, to which 67.7 g of tetrahydrofurane was added and dissolved. While keeping the reaction system at 60° C., 36.9 g of glycidol (the oxirane value=683.7) was gradually dropped and stirred at 70° C. for 10 hours. AV1 and AV2 of the reaction system were 39.6 and 57.3 respectively, revealing that approximately 27 mol% of unreacted monododecyl phosphate, approximately 33 mol% of dodecylglyceryl phosphate which is a diester phosphate and approximately 40 mol% of dodecyldiglyceryl phosphate which is a triester phosphate were produced.

EXAMPLE 27

200 g (0.73 moles) of monododecyl phosphate having a purity of 97% (AV1=210.3, AV2=420.8) was charged into a reactor, to which 750 ml of 1N sodium hydroxide aqueous solution was added and agitated, followed by heating to 80° C. to make a uniform solution, at which the acid value of the reaction system was 42.9. While keeping the reaction system at 80° C., 347 g (3.75 moles) of epichlorohydrin was gradually added and stirred for 4 hours. The acid value of the reaction system was approximately zero, revealing that the reaction was completed. Thereafter, the reaction solution was freeze-dried to obtain non-volatile residue. To the residue, 1000 ml of acetone was added and placed it at 5° C. After one day, separated crystals were collected, followed by recystalization by acetone to obtain 193 g (yield 69.4%) of white crystals of sodium dodecyl-2-hydroxy-3-chloropropyl phosphate.

¹H NMR:

δ 0.8 ppm (t, 3H, —P—OCH₂(CH₂)₁₀CH₃); δ 1.3 ppm (broad s, 20H, —P—OCH₂(C$\underline{H}$₂)₁₀CH₃); δ 3.4–4.1 ppm

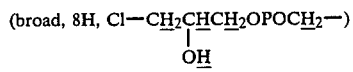

13$_C$ NMR

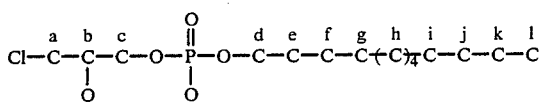

δ (ppm)

1; 14.6, k; 23.5, f; 26.7, g,i: 30.4, h; 30.7, e; 31.6, j; 32.8, a; 45.2, c; 67.0, b; 70.7, d; 72.3

Standard sample: (Si(CH₃)₄
Elementary Analysis:

|  | C (%) | H (%) | P (%) | Na (%) | Cl (%) |
|---|---|---|---|---|---|
| Found | 47.08 | 8.15 | 8.0 | 6.3 | 9.45 |
| Calculated | 47.31 | 8.21 | 8.1 | 6.0 | 9.31 |

TEST EXAMPLE 3

50 g (0.13 moles) of sodium dodecyl-2-hydroxy-3-chloropropyl phosphate obtained in Example 27 was charged into a reactor, followed by reaction with 28.8 g (0.13 moles) of dodecyldimethylamine in a mixed solvent of water and ethanol. The reaction solution was analyzed by HPLC. The chromatography showed no peaks corresponding to the starting material but peaks corresponding to a new reaction product. The product was collected by HPLC and the solvent was distilled off under reduced pressure to obtain sodium dodecyl-2-hydroxy-3-dodecyldimethylammoniumpropyl phosphate.

TEST EXAMPLE 4

10 g (0.026 moles) of dodecyl-2-hydroxy-3-chloropropyl phosphate obtained in Example 27 was charged into a reactor, to which 25 g of water was added, followed by dissolution. To the reaction solution, 6 g of aqueous solution containing 1.0 g of sodium hydroxide was added under agitation while cooling the reactor by iced water, followed by agitation for 1.5 hours. Thereafter, the reaction solution was freeze-dried and subjected to analysis by ¹H-NMR. It showed that little starting material was present, on the other hand, sodium dodecylglycidyl phosphate was produced.

EXAMPLE 28

As the same manner as in Example 27, 200 g (0.55 moles) of monooctadecyl phosphate having a purity of 97% (AV1=160.7, AV2=321.5) was dissolved by 573 ml of 1N potassium hydroxide aqueous solution at 55° C., at which the acid value of the reaction system was 40.3. To the solution, 265 g (2.86 moles) of epichlorohydrin was gradually added and stirred at the temperature for 20 hours. The acid value of the reaction system was approximately zero, revealing that the conversion rate of the phosphoric monoester is almost 100%. The reaction solution was cooled down to the room temperature and was transferred to a fraction funnel. The pH was adjusted to 1 by concentrated HCl. The solution was extracted by 400 ml of ethylether twice, Then mixed up with organic layer, washed five times by 200 ml of water. Thereafter, the solution was extracted by 500 ml of 1N potassium hydroxide aqueous solution twice and the water layer was washed once by 400 ml of ethylether, followed by adjustment of pH to 1 by concentrated HCl. The solution was then extracted twice by 400 ml of ethylether and the ethylether was distilled off under reduced pressure to obtain 198 g (yield 81.2%) of 2-hydroxy-3-chloropropyl phosphate Elementary Analysis:

|  | C (%) | H (%) | P (%) | Cl (%) |
|---|---|---|---|---|
| Found | 56.77 | 9.84 | 7.0 | 8.20 |
| Calculated | 56.94 | 10.01 | 7.0 | 8.00 |

EXAMPLE 29

20 g (0.057 moles) of mono2-hexyldecyl phosphate having a purity of 92% (AV1=167.2, AV2=329.8) was dispersed in 59.6 ml of 1N sodium hydroxide aqueous solution, at which the acid value of the reaction system was 39.5. While keeping the reaction system at 80° C., 16.5 g (0.178 moles) of epichlorohydrin was gradually added, followed by agitation at the temperature for 8 hours. The acid value of the reaction system was approximately zero, revealing that the conversion rate of the phosphoric monoester was almost 100%. The reaction solution was analyzed by HPLC. The chromatography showed peaks corresponding to hydrolysate or epichlorhidrine and a new reaction product. The resulting product was collected by HPLC and the solvent was distilled off under reduced pressure to obtain 20.5 g (yield 82.3%) of sodium 2-hexyldecyl 2-hydroxy-3-chloropropyl phosphate.

Elementary Analysis:

|  | C (%) | H (%) | P (%) | Na (%) | Cl (%) |
|---|---|---|---|---|---|
| Found | 52.05 | 8.79 | 7.1 | 5.8 | 8.37 |
| Calculated | 52.23 | 9.00 | 7.1 | 5.3 | 8.11 |

EXAMPLE 30

20 g (0.043 moles) of mono-2-decyltetradecyl phosphate having a purity of 94% (AV1=134.2, AV2=267.1) was charged into a reactor, to which 47.8 ml of 1N potassium hydroxide aqueous solution was added and agitated, followed by heating to 70° C. to obtain a uniform system, at which the acid value of the reaction system was 37.9. While keeping the reaction system at 70° C., 13.2 g (0.143 moles) of epichrolohydrin was gradually dropped, followed by agitation at the temperature for 20 hours. The acid value of the reaction system was approximately zero, revealing that the reaction rate of phosphoric monoester was almost 100%. The reaction product was collected by HPLC and the solvent was distilled off under reduced pressure to obtain 19.8 g (yield 81.5%) of 2-decyltetradecyl 2-hydroxy-3-chloropropyl phosphate.

Elementary Analysis:

|  | C (%) | H (%) | P (%) | K (%) | Cl (%) |
|---|---|---|---|---|---|
| Found | 52.25 | 8.88 | 6.3 | 8.5 | 7.66 |
| Calculated | 52.43 | 9.01 | 6.4 | 8.1 | 7.37 |

EXAMPLE 31

20 g (0.13 moles) of monobutyl phosphate having a purity of 99% (AV1=360.6, AV2=721.3) was charged into a reactor, to which 129 ml of 1N sodium hydroxide aqueous solution was added and agitated at 70° C. to obtain uniform solution, at which the acid value of the reaction system was 46.7. While keeping the reaction system at 70° C., 59.2 g (0.64 moles) of epichlorohydrin was gradually dropped, followed by agitation at the temperature for 20 hours. The acid value of the reaction system was approximately zero, revealing that the conversion rate of the phosphoric monoester was almost 100%. The resulting product was collected by HPLC and the solvent was distilled off under reduced pressure to obtain 30.2 g (yield 86.5%) of sodium butyl 2-hydroxy-3-chloropropyl phosphate.
Elementary Analysis:

|  | C (%) | H (%) | P (%) | Na (%) | Cl (%) |
|---|---|---|---|---|---|
| Found | 31.14 | 5.38 | 11.2 | 8.9 | 13.55 |
| Calculated | 31.30 | 5.63 | 11.5 | 8.6 | 13.20 |

The results of the analysis of HPLC revealed that the purity was 98 to 99%.

EXAMPLE 32

20 g (0.049 moles) of monotrioxyethylenedodecyl phosphate having a purity of 98% (AV1=142.8, AV2=288.2) was charged into a reactor, to which 50.9 ml of 1N potassium hydroxide aqueous solution was added and agitated at 80° C. to obtain uniform solution, at which the acid value of the reaction system was 39.5. While keeping the reaction system at 80° C., 22.7 g (0.25 moles) of epichlorohydrin was gradually dropped, followed by agitation at the temperature for 6 hours. The acid value of the reaction system was approximately zero, revealing that the reaction rate of the phosphoric monoester was almost 100%. The resulting product was collected by HPLC and the solvent was distilled off under reduced pressure to obtain 19.3 g (yield 74.5%) of potassium trioxyethlenedodecyl 2-hydroxy-3-chloropropyl phosphate.
Elementary Analysis:

|  | C (%) | H (%) | P (%) | K (%) | Cl (%) |
|---|---|---|---|---|---|
| Found | 47.39 | 7.95 | 5.9 | 7.3 | 6.99 |
| Calculated | 47.68 | 8.14 | 5.9 | 7.4 | 6.72 |

The HPLC analysis revealed the purity of 98 to 99%.

EXAMPLE 33

20 g (0.060 moles) of monononylphenyl phosphate having a purity of 90% (AV1=168.2, AV2=338.2) was charged into a reactor, to which 60.0 ml of 1N potassium hydroxide aqueous solution was added and agitated, followed by dispersing uniformly at 80° C., at which the acid value of the reaction system was 42.3. While keeping the reaction system at 80° C., 27.8 g (0.30 moles) of epichlorohydrin was gradually dropped, followed by agitation at the temperature for 6 hours. The acid value of the reaction system was approximately zero, revealing that the reaction rate of the phosphric monoester was almost 100%. The resulting product was clollected by HPLC and the solvent was distilled off under reduced pressure to obtain 18.1 g (yield 70.0%) of potassium nonylphenyl 2-hydroxy-3-chloropropyl phosphate.
Elementary Analysis:

|  | C (%) | H (%) | P (%) | K (%) | Cl (%) |
|---|---|---|---|---|---|
| Found | 49.83 | 6.56 | 7.3 | 9.0 | 8.59 |
| Calculated | 50.17 | 6.78 | 7.2 | 9.1 | 8.23 |

The results of the analysis of HPLC revealed that the purity was 98 to 99%.

EXAMPLE 34

20 g (0.052 moles) of monooctadecenyl phosphate having a purity of 90% (AV1=165.0, AV2=323.2) was charged into a reactor, to which 58.8 ml of 1N potassium hydroxide aqueous solution was added and agitated at 80° C. to obtain uniform solution, at which the acid value of the reaction system was 40.2. While keeping the reaction system at 80° C., 24.1 g (0.26 moles) of epichlorohydrin was gradually dropped, followed by agitation at the temperature for 6 hours. The acid value of the reaction system was approximately zero, revealing that the reaction rate of the phosphoric monoester was almost 100%. The resulting product was collected by HPLC and the solvent was distilled off under reduced pressure to obtain 16.9 g (yield 67.8%) of potassium octadecenyl 2-hydroxy-3-chloropropyl phosphate.
Elementary Analysis:

|  | C (%) | H (%) | P (%) | K (%) | Cl (%) |
|---|---|---|---|---|---|
| Found | 52.08 | 8.52 | 6.5 | 8.1 | 7.63 |
| Calculated | 52.65 | 8.63 | 6.5 | 8.2 | 7.40 |

The HPLC analysis revealed the purity of 98 to 99%.
What is claimed is:

1. A process for preparing an alkali metal salt of a phosphoric ester having the formula (III):

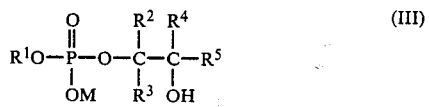

wherein $R^1$ is an organic group selected from one of the following groups:
(i) a linear or branched, alkyl or alkenyl group having 8 to 36 carbon atoms,
(ii) an alkyl phenyl group having an alkyl group of 4 to 14 carbon atoms,
(iii) a polyoxyalkylene alkyl, alkenyl or alkylphenyl group, wherein said polyoxyalkylene is either 1 to 20 moles of an oxyethylene, oxypropylene or oxyethylene-propylene addition group, said alkyl or alkenyl having 8 to 36 carbon atoms, and said alkylphenyl group having 4 to 14 carbon atoms,
(iv) a 2-hydroxyalkyl group having 10 to 38 carbon atoms,
(v) a 2-hydroxy-3-alkyloxypropyl group, wherein said alkyl group has 8 to 36 carbon atoms, (vi) a fluorine-containing alkyl group having 8 to 36 carbon atoms, and (vii) an active hydrogen residue of pentose or hexose; and $R^2$, $R^3$, $R^4$ and $R^5$ each individually represents a hydrogen atom or an organic group as defined below, or $R^2$ and $R^4$ are coupled together to form a ring, and M represents an alkali metal, which process comprises:

(A) reacting a monoalkali metal salt of an organophosphoric monoester, having the formula (I):

wherein $R^1$ and M have the above defined meaning, with an epoxy compound having the formula (II):

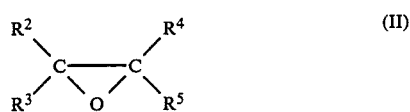

wherein $R^2$, $R^3$, $R^4$ and $R^5$ are each hydrogen or an organic group such that the epoxy compound is selected from the group consisting of glycidyl(meth)acrylate, allyl glycidyl ether, alkyl glycidyl ethers, glycidyltrialkyl ammonium halide and the diglycidyl ether of bisphenol A, epichlorohydrin, glycidol and the epoxides of α-olefins and bis(3,4-epoxy-6-methylcyclohexylmethyl)adipate.

2. A process for preparing an alkali metal salt of a phosphoric ester having the formula (IV):

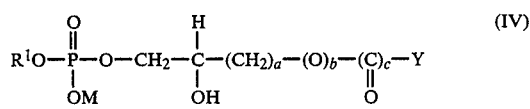

wherein Y is a hydrogen atom, a halogen atom, a hydroxy group, an alkyl or alkenyl group of 1 to 36 carbon atoms which is unsubstituted or is partially substituted by one or more fluorine atoms or an alkylphenyl group having a $C_1$–$C_{15}$ alkyl group, a has a value of 0 to 2, b and c each have a value of 0 or 1, M is an alkali metal, and $R^1$ is an organic group selected from one of the following groups:

(i) a linear or branched, alkyl or alkenyl group having 8 to 36 carbon atoms, (ii) an alkylphenyl group having an alkyl group of 4 to 14 carbon atoms, (iii) a polyoxyalkylene alkyl, alkenyl or alkylphenyl group, wherein said poloxyalkylene is 1 to 20 moles of an oxyethylene, oxopropylene or oxyethylenepropylene addition group, said alkyl or alkylene having 8 to 36 carbon atoms, and said alkylphenyl group having 4 to 14 carbon atoms, (iv) a 2-hydroxyalkyl group having 10 to 38 carbon atoms, (v) a 2-hydroxy-3-alkyloxypropyl group, wherein said alkyl group has 8 to 36 carbon atoms, (vi) a fluorine-containing alkyl group having 8 to 36 carbon atoms, and (vii) an active hydrogen residue of pentose or hexose; which process comprises:

(A) reacting a monoalkali metal salt of an organophosphoric monoester, having the formula (I):

wherein $R^1$ and M have the above defined meanings with an epoxy compound having the following formula (V):

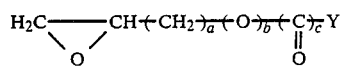

wherein Y, a, b and c have the above defined meanings.

3. A process for preparing an alkali metal salt of a phosphoric ester having the following formula (VI):

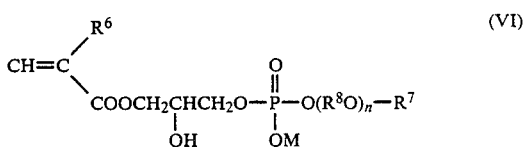

wherein $R^6$ is a hydrogen atom or methyl group, $R^7$ is a linear or branched alkyl group of 1 to 36 carbon atoms, which is unsubstituted or substituted by one or more fluorine atoms, or a phenyl group which is unsubstituted or substituted by linear or branched alkyl groups of 1 to 15 carbon atoms, $R^8$ is an alkylene group of 2 to 3 carbon atom, n is a number of from 0 to 30 and M is an alkali metal, which process comprises:

(A) reacting a salt of a phosphoric monoester, having the following formula (VII):

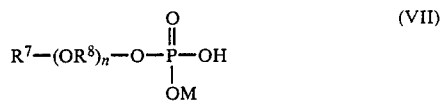

wherein $R^7$, $R^8$, n and M have the above defined meanings, with a compound having the following formula (VIII):

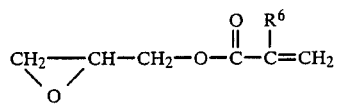

wherein $R^6$ has the above defined meaning.

4. The process according to claim 1, wherein said epoxy compound is glycidyl(meth)acrylate or allyl glycidyl ether.

5. The process according to claim 1, wherein said epoxy compound is reacted with said monoalkali metal salt of the organophosphoric monoester at a temperature in the range of 30°–100° C., in the amount of 1–10 moles of epoxy compound per mole of monoalkali metal salt of the organophosphoric monoester.

6. The process according to claim 1, wherein said alkali metal is sodium or potassium.

7. The process according to claim 5, wherein said epoxy compound is reacted with said monoalkali metal salt of the organophosphoric monoester at a temperature in the range of 50°–90° C., in the amount of 3–5 moles of epoxy compound per mole of monoalkali metal salt of the organophosphoric monoester.

8. The process according to claim 2, wherein said epoxy compound is reacted with said monoalkali metal salt of the organophosphoric monoester at a temperature in the range of 30°-100° C., in the amount of 1-10 moles of epoxy compound per mole of monoalkali metal salt of the organophosphoric monoester.

9. The process according to claim 3, wherein said epoxy compound is reacted with said monoalkali metal salt of the organophosphoric monoester at a temperature in the range of 30°-100° C., in the amount of 1-10 moles of epoxy compound per mole of monoalkali metal salt of the organophosphoric monoester.

* * * * *